(12) United States Patent
Fredericksen et al.

(10) Patent No.: US 7,508,226 B2
(45) Date of Patent: Mar. 24, 2009

(54) VERSATILE MATERIALS PROBE

(75) Inventors: Ross T. Fredericksen, Mantorville, MN (US); Don A. Gilliland, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 218 days.

(21) Appl. No.: 11/551,062

(22) Filed: Oct. 19, 2006

(65) Prior Publication Data
US 2008/0094083 A1    Apr. 24, 2008

(51) Int. Cl.
*G01R 31/02* (2006.01)
(52) U.S. Cl. ............................................. 324/754
(58) Field of Classification Search ................ 324/754, 324/761–762, 765, 158.1; 439/581, 578, 439/942; 250/310–311
See application file for complete search history.

(56) References Cited

U.S. PATENT DOCUMENTS

| 5,371,469 | A | 12/1994 | Anderson |
| 6,147,851 | A | 11/2000 | Anderson |
| 6,462,570 | B1 * | 10/2002 | Price et al. ................. 324/754 |
| 7,292,059 | B2 * | 11/2007 | Devey et al. ................. 324/771 |

* cited by examiner

*Primary Examiner*—Ha Tran T Nguyen
*Assistant Examiner*—Tung X Nguyen
(74) *Attorney, Agent, or Firm*—Cantor Colburn LLP

(57) ABSTRACT

Disclosed is an electrical measurement probe including two probe blocks, each probe block having a connection face and a measurement face. Each probe block also includes a plurality of spring loaded pogo pins. Each pogo pin has a first end that extends to the connection face and a second end that protrudes from the measurement face. The two probe blocks are attached to a top plate. The top plate is attached to a face of each probe block opposite to the measurement face of the probe block.

7 Claims, 5 Drawing Sheets

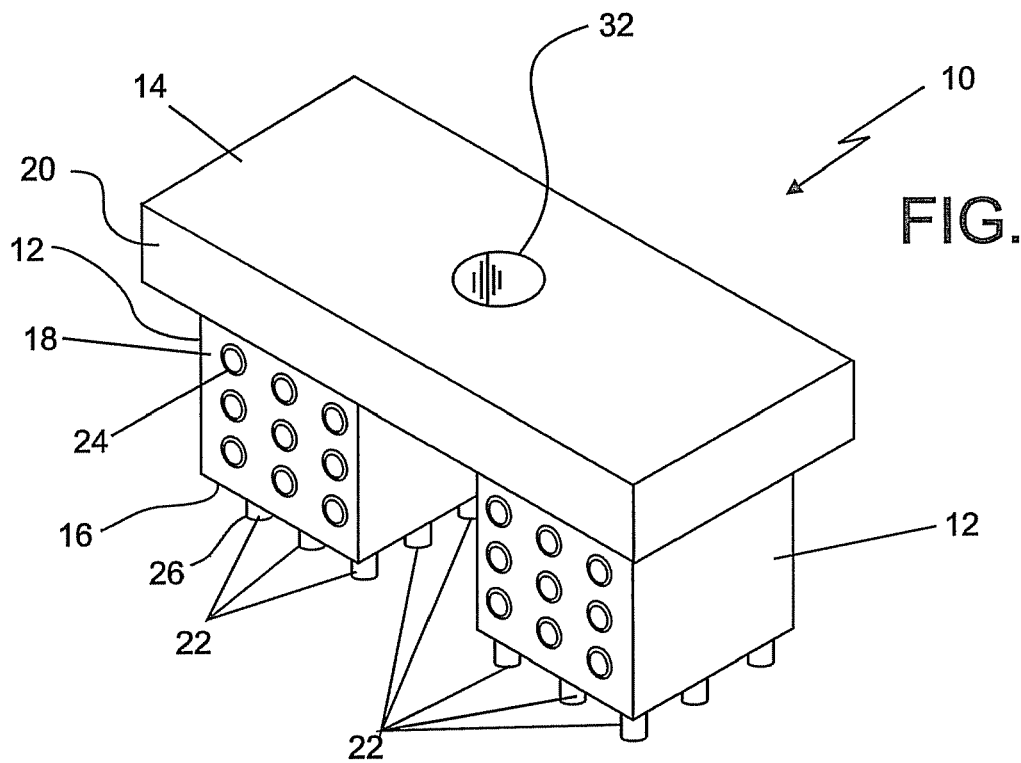
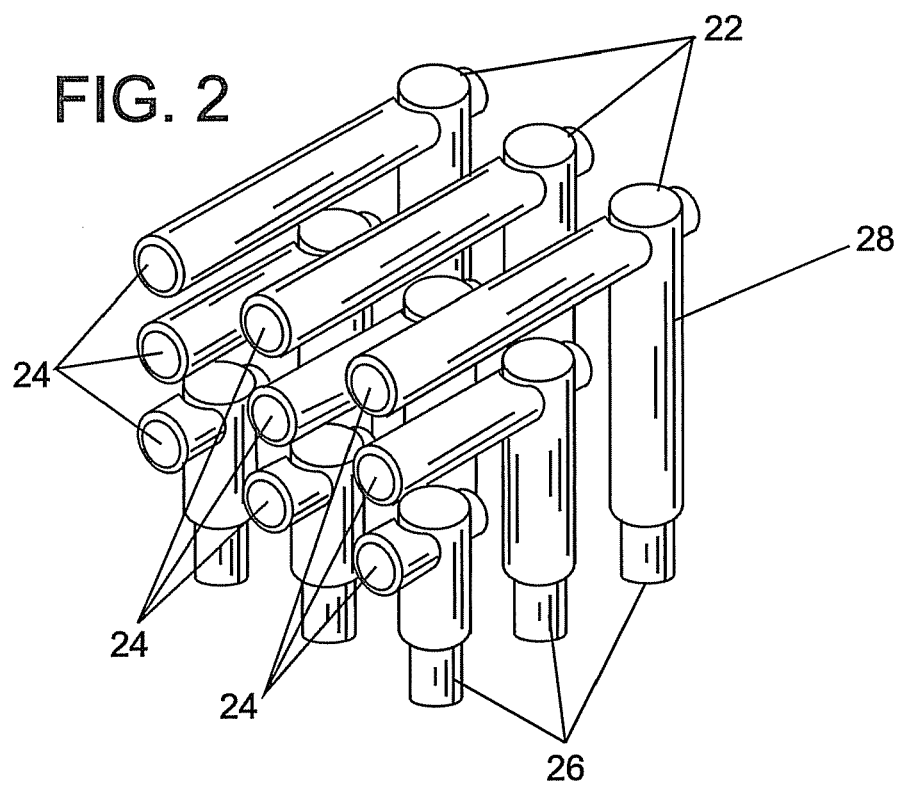

VERSATILE MATERIALS PROBE

TRADEMARKS

IBM® is a registered trademark of International Business Machines Corporation, Armonk, N.Y., U.S.A. Other names used herein may be registered trademarks, trademarks or product names of International Business Machines Corporation or other companies.

BACKGROUND OF THE INVENTION

1. Field of the Invention

This invention relates to measurement of material properties, and particularly to a versatile probe for measuring electrical impedance of materials.

2. Description of Background

The composition of materials used in electronic devices is determined for a variety of reasons. For example, a European Union directive, "Restriction of Hazardous Substances" (RoHS), bans the placing on the EU market of new electrical and electronic equipment containing more than agreed levels of lead, cadmium, mercury, hexavalent chromium, polybrominated biphenyl (PBB) and polybrominated diphenyl ether (PBDE) flame retardants, and material composition is determined to ensure compliance with RoHS. One method of determining the material composition is by measuring the electrical impedance of the material. Traditionally, such impedance measurements have been accomplished through the use of a single-point or surface probe resulting in an impedance value of the material measured in ohms/square.

A measurement is performed by placing the single-point or surface probe on the material. The measurement can be influenced by an amount of force applied to the probe when placing it on the surface. However, the measured impedance can be erroneously high or low if the applied force is not sufficiently controlled. Furthermore, when taking several measurements on a material sample, the applied force must be consistent to ensure the measured impedance values are comparable. In a traditional probe, a nickel plated gasket surrounds the probe and is intended to control the amount of force applied to the probe. The gasket, however, wears or changes characteristics over time requiring its replacement. Additionally, the gasket often deforms to a compressed state over time which can influence the amount of force applied to the probe, thereby changing the impedance measurements.

Finally, the standard probe is limited to talking one particular type of measurement (e.g. ohms/square) and only one measurement at a time. To measure more than one location on a sample, the probe must be moved. To take measurements requiring more than one interface to the material sample, more than one probe or some additional devices must be used in addition to the standard probe.

What is needed is a measurement probe that can accurately control the force applied to the probe during measurement. In addition, a probe is needed that is versatile, allowing for many measurements to be performed without moving the probe, and allowing for differing types of measurements to be performed without the use of additional probes or other ancillary equipment to facilitate the measurement.

SUMMARY OF THE INVENTION

The shortcomings of the prior art are overcome and additional advantages are provided through the provision of an electrical measurement probe comprising two probe blocks, each probe block having a connection face and a measurement face. Each probe block includes a plurality of spring loaded pogo pins. Each pogo pin having a first end that extends to the connection face and a second end that protrudes from the measurement face. The two probe blocks are attached to a top plate. The top plate is attached to a face of each probe block opposite to the measurement face of the probe block.

Additional features and advantages are realized through the techniques of the present invention. Other embodiments and aspects of the invention are described in detail herein and are considered a part of the claimed invention. For a better understanding of the invention with advantages and features, refer to the description and to the drawings.

TECHNICAL EFFECTS

As a result of the summarized invention, technically we have achieved a solution which improves measurement versatility by providing a plurality of electrically conductive pogo pins, and improves measurement accuracy and repeatability by controlling the maximum travel of each of the spring loaded pogo pins.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 illustrates a side view of one example of a versatile materials probe.

FIG. 2 is a perspective view of a plurality of L-shaped pogo pins.

Figure 3:
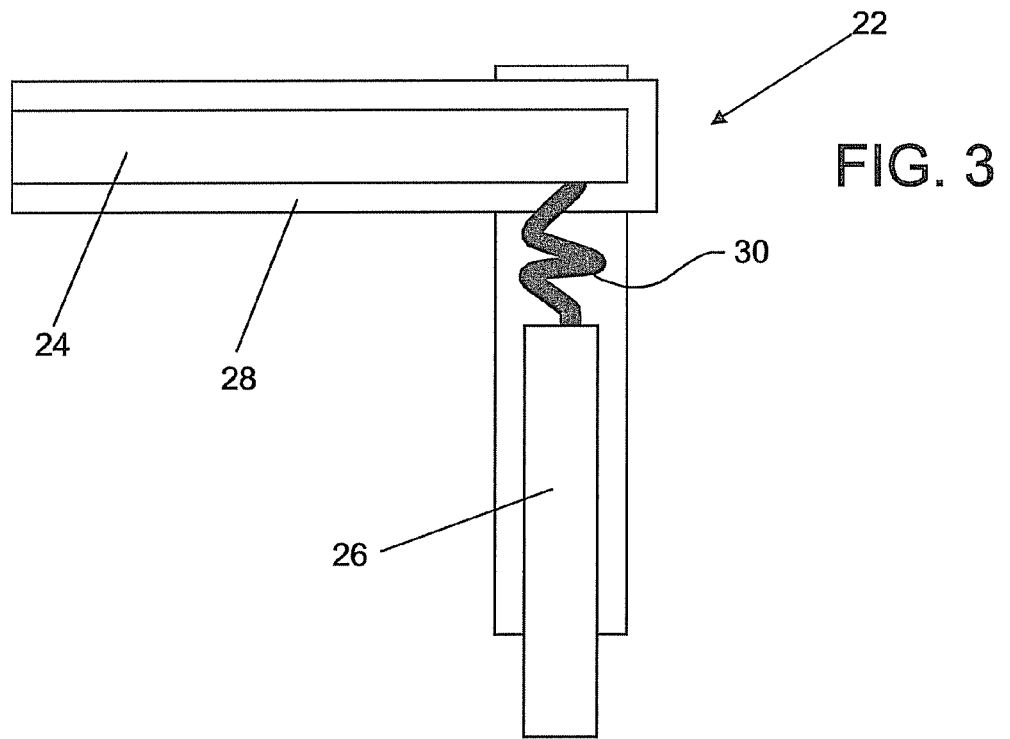
FIG. 3 is a section view of an L-shaped pogo pin.

The detailed description explains the preferred embodiments of the invention, together with advantages and features, by way of example with reference to the drawings.

DETAILED DESCRIPTION OF THE INVENTION

Turning now to the drawings in greater detail, it will be seen that in FIG. 1 there is an improved materials probe 10. The probe 10 comprises a pair of probe blocks 12 connected to a top plate 14. Each probe block 12 is cube-shaped and comprises a measurement face 16 opposite the face of the probe block 12 which is connected to the top plate 14, and a connection face 18 which is adjacent to the measurement face 16 and substantially parallel to a longitudinal face 20 of the top plate 14.

Each probe block 12 contains an array of commercially available pogo pins 22. Each pogo pin 22 is formed from a conductive material and, for example, is nickel plated. Referring to FIG. 2, the pogo pins 22 are L-shaped and comprise a fixed end 24 and a moveable end 26 enclosed in a shell 28. As shown in FIG. 3, the moveable end 26 is spring-loaded, and electrical connection between the moveable end 26 and the fixed end 24 is provided by a spring 30. Returning now to FIG. 1, the fixed end 24 of each pogo pin 22 is disposed on the connection face 18, and the moveable end 26 of each pogo pin 22 is disposed through the measurement face 16. Spring-loading the moveable end 26 allows the pogo pins 22 to absorb force applied to the probe 10 when measuring a material.

Figure 4:
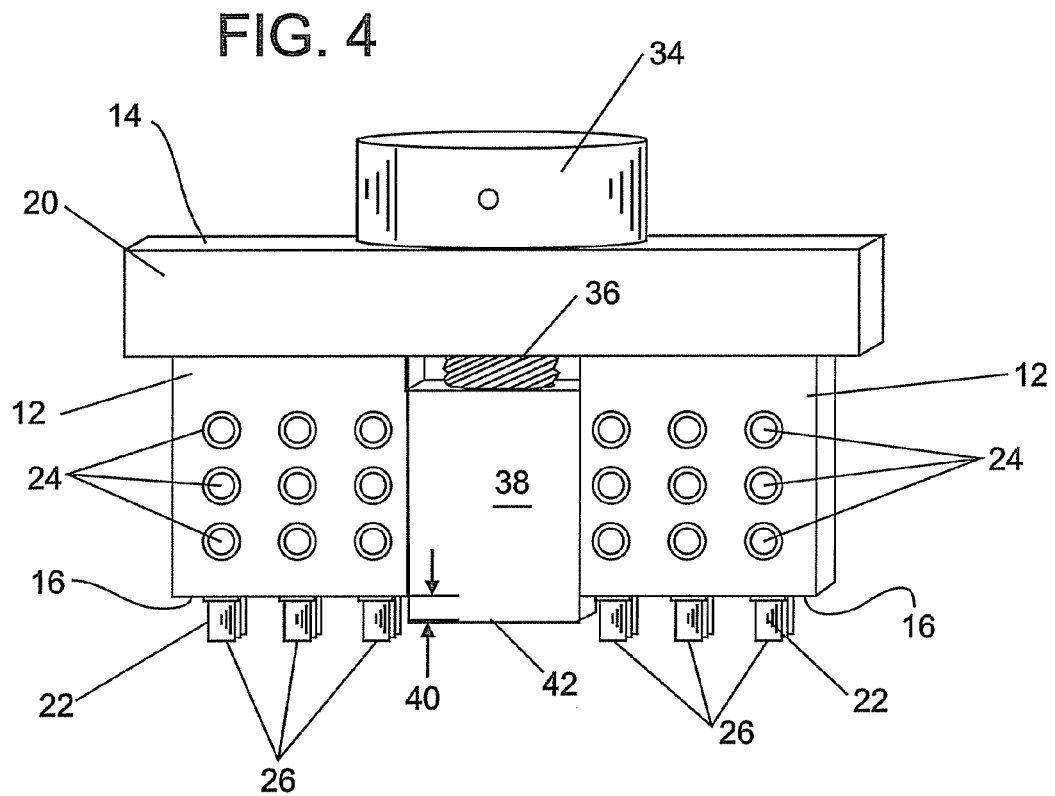
FIG. 4 illustrates a perspective view of one example of a versatile materials probe including an adjustment knob.

The top plate 14 includes a through hole 32. As shown in FIG. 4, an adjustment knob 34 is disposed on top of the top plate 14. A threaded portion 36 extends from a bottom face of the adjustment knob 34 and through the hole 32 in the top plate 14 and further extends between the two probe blocks 12. An adjustment block 38 is disposed between the two probe blocks 12 and includes a threaded hole on its top face. The threaded portion 36 is threaded into the adjustment block 38, so that when the adjustment knob 34 is turned in a clockwise direction, the adjustment block 38 is raised toward the top plate 14 and when the adjustment knob 34 is turned in a counter clockwise direction, the adjustment block 38 is lowered away from the top plate 14.

The height of the adjustment block 38 relative to the measurement face 16 controls the amount of force applied when a measurement is taken. The greater an offset 40 between a stop face 42 and the measurement face 16, the smaller the distance that the moveable ends 26 of the pogo pins 22 will travel before the stop face 42 rests on the material, and the lower the amount of force. Conversely, the smaller the offset 40, the greater the distance moveable ends 26 of the pogo pins 22 will travel, and the greater the amount of force. Incorporation of the adjustment block 38 ensures that substantially equal amounts of force are applied when taking measurements, resulting in more accurate measurements since a known source of error (a variation in force applied to the probe) has been removed.

Figure 5:
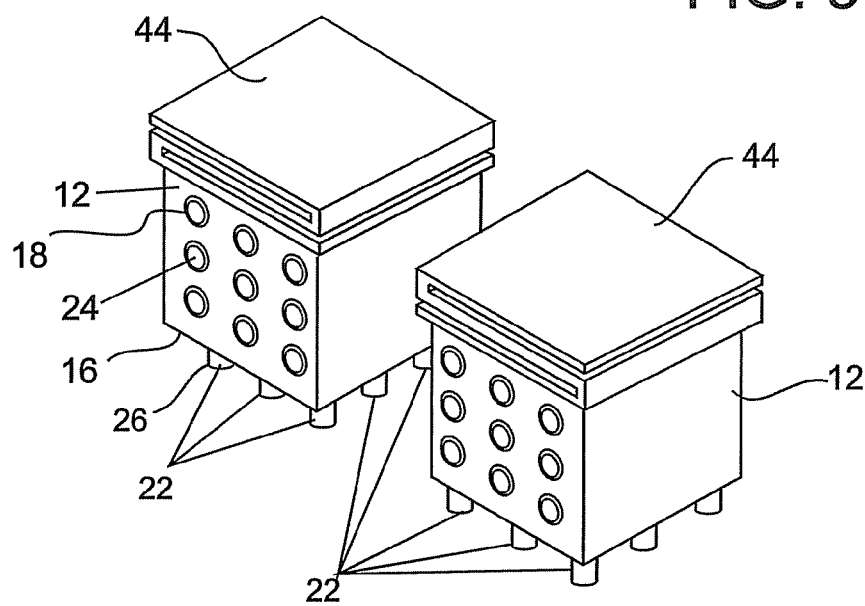
FIG. 5 illustrates one example of load cells attached to the probe blocks.

To set the applied force to a known value, as shown in FIG. 5, a load cell 44 can be fitted to each probe block 12. When pressure is applied to the pogo pins 22, the pressure is measured as strain in the load cell 44. The strain measurement is outputted and translated into a force value. The position of the adjustment block 38 can be adjusted until the desired force value is measured.

Figure 6:
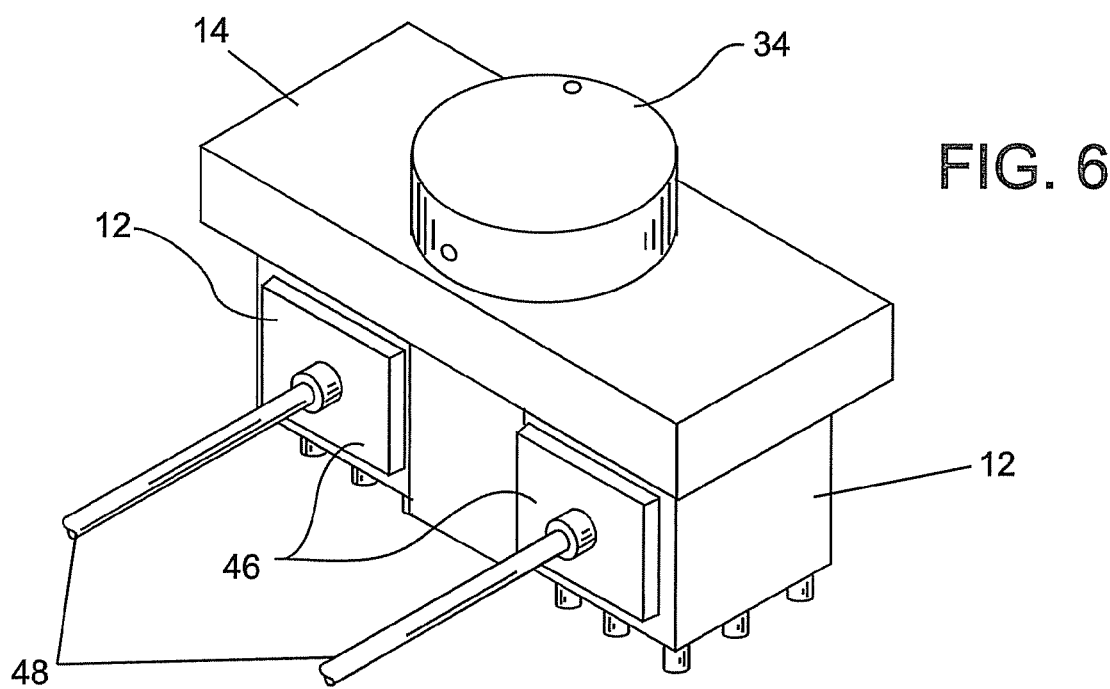
FIG. 6 illustrates one example of a versatile probe configured for ohms/square measurement.
Figure 7:
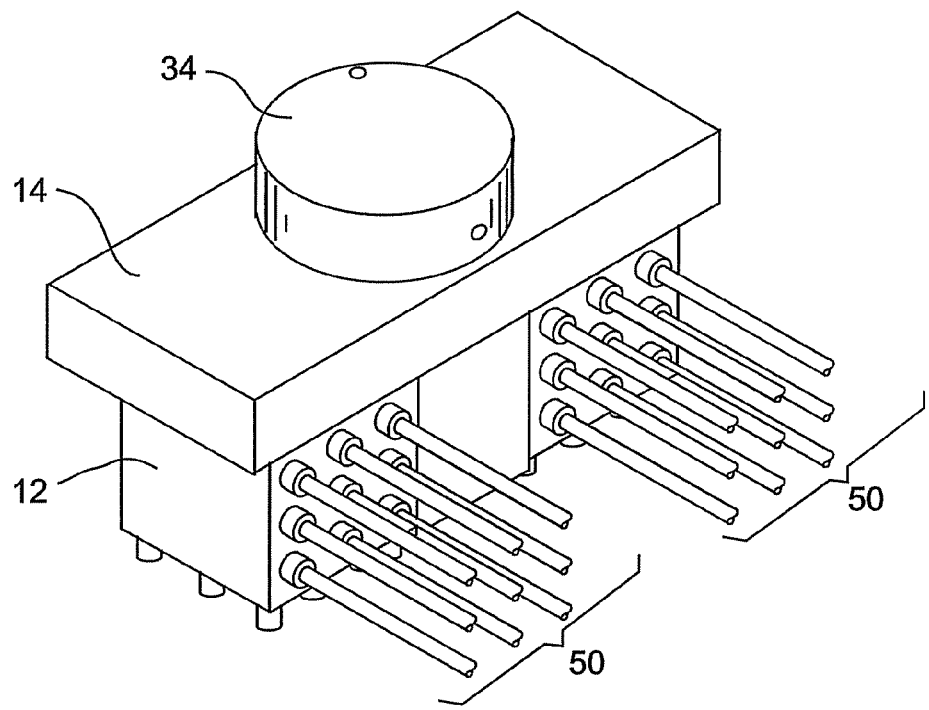
FIG. 7 illustrates one example of a versatile probe configured for statistical data collection.

The number of pogo pins 22 in the probe blocks 12 allows the probe 10 to be configured to perform a variety of measurements. For example, as shown in FIG. 6, by configuring each probe block 12 with one connection plate 46 on the connection face 18, the fixed ends 24 of the pogo pins 22 in each probe block 12 are connected to a single lead wire 48. With this configuration, the probe 10 is able to provide a measurement similar to a conventional ohms/square probe. Alternatively, and as shown in FIG. 7, if individual connections 50 are provided to the fixed ends 24 of each pogo pin 22, multiple measurements can be obtained and statistically combined to obtain, for example, mean and standard deviation of the measurements without moving the probe. This configuration also allows for connection of the probe 10 to a voltage network analyzer, and a number of measurements may be performed without moving the probe 10.

Figure 8:
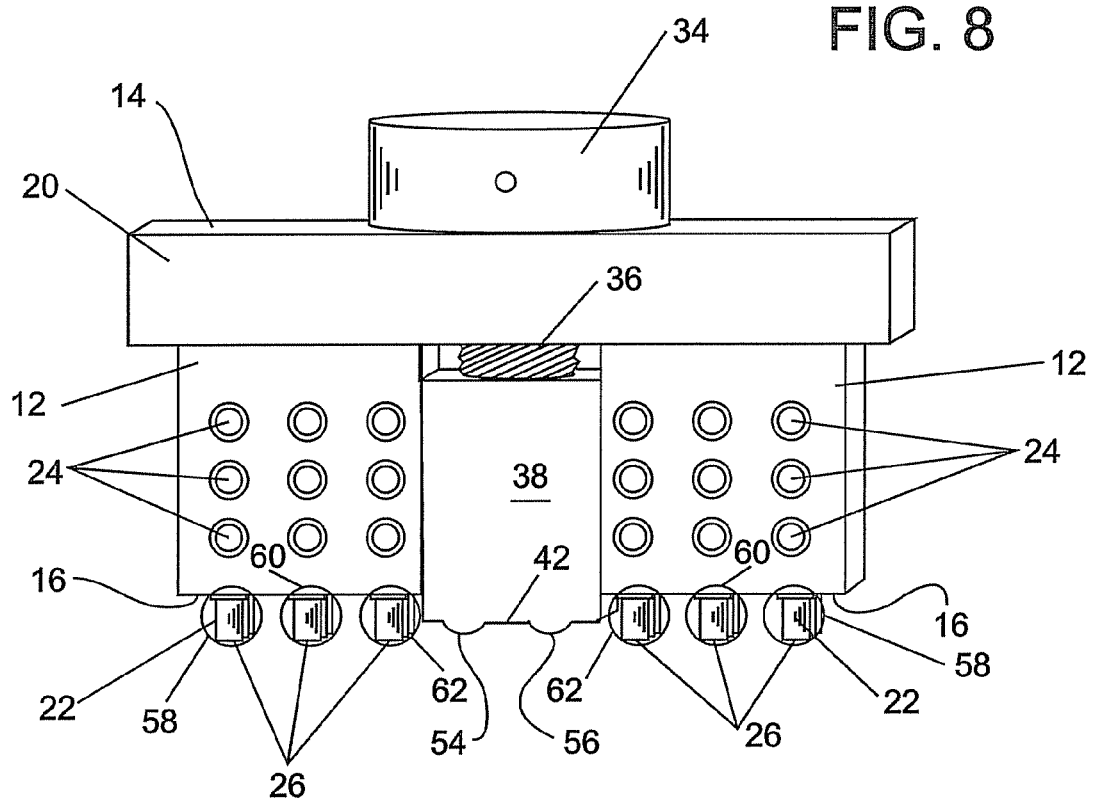
FIG. 8 illustrates one example of a versatile probe configured for measurement using an Anderson loop method.

In one embodiment, the probe 10 is configured to test the impedance of one material compared to the impedance of a reference material. To have this capability, as shown in FIG. 8, an electrically conductive contact plate 52 is disposed at the stop face 42. When comparing the impedance of two materials, a first probe block 12a is applied to a first material, a second probe block 12b is applied to a second material, and the contact plate 52 is disposed such that a first rib 54 contacts the first material and a second rib 56 contacts the second material. The provision of the contact plate 52 enables the probe 10 to compare the impedance of two materials via an Anderson loop method. In this case, a first row 58 of pogo pins 22 of each probe block 12 provides current injection or removal, a second row 60 and a third row 62 of pogo pins 22 of each probe block 12 are used to measure the voltage drop in each material, and the contact plate 52 provides current continuation between the first material and the second material. The resulting measured voltage drop across each material can be compared to determine the materials' relative impedance.

Figure 9:
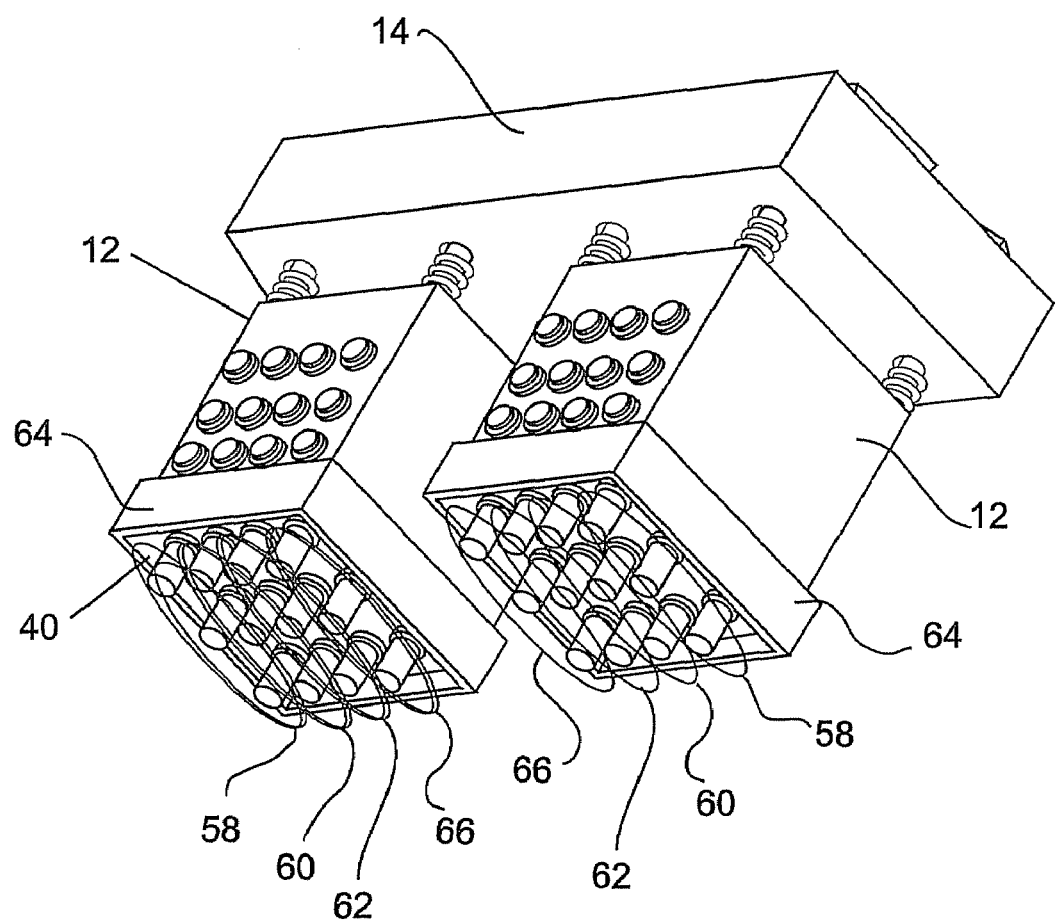
FIG. 9 illustrates an alternative embodiment of a versatile probe configured for measurement using an Anderson loop method.

FIG. 9 illustrates another embodiment of the probe 10 that may be configured to test the impedance of one material compared to a reference material. In this embodiment, each probe block 12 requires at least twelve pogo pins 22 disposed in four rows of three pogo pins 22 each. In this embodiment, there is no adjustment block 38 between the probe blocks 12, so the probe blocks 12 can move independently. When comparing the impedance of two materials, a first probe block 12a is applied to a first material, and a second probe block 12b is applied to a second material. Because the two probe blocks 12a and 12b can move independently, the first material and the second material can be of different thicknesses. In order to control the force applied to the probe in this instance, each probe block 12a and 12b includes a sleeve 64 which extends from the measurement face 16. The sleeve 64 is disposed with an offset 40 to the measurement face 16 to control the amount of force applied as described above. To measure impedance, this embodiment may utilize an Anderson loop method. In this case, a first row 58 of pogo pins 22 of each probe block 12 provides current injection or removal, a second row 60 and a third row 62 of pogo pins 22 of each probe block 12 are used to measure the voltage drop in each material, and a fourth row 66 provides current continuation between the first material and the second material. The resulting measured voltage drop across each material can be compared to determine the materials' relative impedance.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. An electrical measurement probe comprising:
a first probe block and a second probe block, each having a connection face and a measurement face;
each probe block further comprising a plurality of spring loaded electrically conductive pogo pins, respectively disposed through the connection face and the measurement face;
a top plate connected to a face of both probe blocks opposite to the measurement face;
a through hole in the top plate;
an adjustment knob disposed on a face of the top plate opposite the first and second probe blocks, the adjustment knob having a threaded end extending through the through hole and between the first and second probe blocks; and
an adjustment block having a threaded hole, the adjustment block being threaded onto the threaded end of the adjustment knob between the two probe blocks, the position of the adjustment block determining the maximum amount of travel of the second end of each pogo pin of the pluralities of pogo pins.

2. The probe of claim 1 wherein a load cell for calibrating the probe is disposed between each probe block and the top plate.

3. The probe of claim 1 wherein the adjustment block includes an electrically conductive contact plate disposed substantially parallel to the measurement face.

4. The probe of claim 1 wherein the connection face is orthogonal to the measurement face.

5. The probe of claim 3 wherein each pogo pin is L-shaped and comprises a moveable end and a fixed end electrically connected by a spring and disposed in a shell, the moveable end protruding through the measurement face and the fixed end protruding through the connection face.

6. The probe of claim 1 wherein each connection face includes a connector for a single lead wire providing electrical communication to and from each plurality of pogo pins.

7. The probe of claim 1 wherein each plurality of pogo pins has at least nine pogo pins and each connection face includes at least nine connectors for lead wires providing electrical communication to and from each plurality of pogo pins.

* * * * *